US010973623B1

(12) United States Patent
Zhukauskas

(10) Patent No.: US 10,973,623 B1
(45) Date of Patent: Apr. 13, 2021

(54) SURGICAL IMPLANTS USEFUL IN ORTHOPEDIC SURGERY

(71) Applicant: RTI Surgical, Inc., Alachua, FL (US)

(72) Inventor: Arunas Antano Zhukauskas, Gainesville, FL (US)

(73) Assignee: RTI Surgical, Inc., Alachua, FL (US)

(*) Notice: Subject to any disclaimer, the term of this patent is extended or adjusted under 35 U.S.C. 154(b) by 56 days.

(21) Appl. No.: 15/639,890

(22) Filed: Jun. 30, 2017

Related U.S. Application Data

(60) Provisional application No. 62/357,575, filed on Jul. 1, 2016.

(51) Int. Cl.
*A61F 2/08* (2006.01)

(52) U.S. Cl.
CPC .............. *A61F 2/0811* (2013.01); *A61F 2/08* (2013.01); *A61F 2002/087* (2013.01); *A61F 2002/0888* (2013.01); *A61F 2240/002* (2013.01)

(58) Field of Classification Search
CPC ............ A61F 2/0811; A61F 2002/0817; A61F 2002/0847; A61F 2002/0858; A61F 2002/087; A61F 2/08; A61F 2002/0888
See application file for complete search history.

(56) References Cited

U.S. PATENT DOCUMENTS

| 5,320,115 A * | 6/1994 | Kenna ................ A61B 17/1615 128/898 |
| 2013/0096612 A1* | 4/2013 | Zajac ................ A61B 17/0401 606/232 |

OTHER PUBLICATIONS

ACL Reconstruction with BTB TightRope® Graft Fixation. Surgical Technique. Copyright 2017 Arthrex, Inc.

* cited by examiner

*Primary Examiner* — Christopher D. Prone
(74) *Attorney, Agent, or Firm* — McAndrews, Held & Malloy, Ltd.

(57) ABSTRACT

The present application is directed to the field of surgical implants useful in orthopedic surgery. In one aspect, the present application provides a novel, preshaped allograft or xenograft bone tendon (BT) or bone tendon bone graft (BTB) having at least a portion of the tendon that is wider than the bone blocks. Such preshaped grafts allow for more efficacious surgeries and reduced surgical time.

8 Claims, 14 Drawing Sheets

SURGICAL IMPLANTS USEFUL IN ORTHOPEDIC SURGERY

RELATED APPLICATIONS

The present application claims priority to U.S. Prov. Pat. App. Ser. No. 62/357,575 filed Jul. 1, 2016. That application is incorporated herein by reference in its entirety.

FEDERALLY SPONSORED RESEARCH OR DEVELOPMENT

[Not Applicable]

FIELD OF TECHNOLOGY

The present application is directed to the field of surgical implants useful in orthopedic surgery. In one aspect, the present application provides a novel, preshaped allograft or xenograft bone tendon (BT) or bone tendon bone graft (BTB) having at least a portion of the tendon that is wider than the bone blocks. Such preshaped grafts allow for more efficacious surgeries and reduced surgical time.

BRIEF SUMMARY

In one aspect, the application is directed to a surgical implant useful in orthopedic surgery comprising at least one cut, shaped or machined portion and at least one natural anatomic portion derived from an animal. The cut, shaped or machined portion comprises at least one bone portion having a length, a width and a height and at least two opposing sides running along said length or said height or said width of said bone portion; wherein said bone portion is cut, shaped or machined to fit into a bone tunnel. The at least one cut, shaped or machined portion further comprises at least one tendon portion having a length, a width and a height; where the tendon portion is cut, shaped or machined to allow the tendon to wrap around at least part of said at least two opposing sides and to fit into a bone tunnel when so wrapped. The natural anatomic portion is derived from an animal and comprises at least one region of natural attachment between a bone portion and a tendon portion.

The present application is further directed to implants or grafts where, at its widest point, the width of the tendon or tendon portion is at least 1.5 times the width of the bone block or bone portion. In one aspect, the bone block or bone portion comprises a cross-sectional profile or multiple profiles, in one or more directions, which may vary at different points along the bone block, selected from the group consisting of semi-circular, semi-ovular, triangular, trapezoidal, polygonal, irregular, rectangular, square, curvilinear, and combinations thereof.

The present application is further directed to an allograft or xenograft bone tendon bone graft for use in orthopedic surgery in humans comprising: (a) a bone block having a width defined by two or more cut surfaces and a length, (b) a tendon having a width defined by two or more natural or trimmed edges and a length, (c) a naturally occurring attachment between the tendon and the bone block, (d) at least one free side of the tendon, extending along said length of the tendon and making up a portion of the width of the tendon which is greater than the width of the bone block. The free side of the tendon extends along the length of the tendon and beyond the length of the bone block, and the tendon and the bone block are preshaped for insertion into a bone tunnel wherein at least a portion of the free side of the tendon can be folded or wrapped around. In another aspect, the free side of the tendon wraps around at least a portion of the bone block.

While the bone block width may be defined by two or more cut surfaces, it is understood that such surfaces may be distinct, discontinuous or continuous in relation to each other and that surfaces may include, without limitation, flat, curved, curvilinear, circular, cylindrical, or irregular shapes. Depending on the surfaces involved the measurement may be taken from an endpoint, a boundary, and edge, a tangent point, an inflection point, or some other geometric feature appropriate to define the width. In one aspect the two or more cut surfaces may comprise two distinct and discontinuous opposing flats created by a straight cut, broach, deformation or separation of bone material on each respective side. In another aspect the two or more cut surfaces may comprise two sections of a single or multiple continuous or discontinuous surface or surfaces such as a cylinder created by an oscillatory or rotational cutting tool and either with or without a natural or man-made break, cut or additional surface being present between the two surfaces. In some cases the width of the bone block will be defined as the widest such measurement available at a given point, cross section or region and between two surfaces or between opposing edges of such surfaces, or between points or lines of intersection between such surfaces. In certain cases a width may be defined by measurement between specified points, lines or surfaces which is about equal to or less than the widest possible measurement at that location. This discussion of width measurements may also be applied when appropriate to length, depth, height or other measurements.

The present application is further directed to implants or grafts where the bone block or bone portion comprises a further preshaped feature created to accommodate the tendon or tendon portion when wrapped around for placement of said implant into a human patient. In another aspect, the bone block or bone portion comprises a further preshaped feature created to aid in placement or fixation of the graft. In a further aspect, the bone block or bone portion comprises a tapered, recessed, undercut, flattened or hollow section.

The present application is further directed to an allograft or xenograft surgical implant useful in orthopedic surgery comprising a tendon naturally attached to a preshaped bone block; where the preshaped bone block has a width, and the width of the preshaped bone block is less than said width of the tendon. The tendon contains at least one surface formed by separation of the tendon from a portion of bone which had been attached to and contiguous with the preshaped bone block, and the preshaped bone block contains at least one surface formed by separation of the preshaped bone block from a portion of bone which had been attached to and contiguous with the tendon.

The present application is further directed to an allograft bone tendon bone graft for use in orthopedic surgery in humans comprising two bone blocks connected by a tendon and having a natural attachment between the tendon and the bone blocks maintained along one side of said bone blocks. The tendon comprises at least one section having a width greater than the width of the bone blocks. Further, the bone blocks are preshaped for implantation in a bone tunnel during surgery.

The present application is further directed to bone tendon (BT) or bone tendon bone (BTB) grafts where the width of the tendon is maintained for its full length. In other aspects, the width of the tendon is maintained for at least half its length. In other aspects, the width of the tendon varies proportionally, linearly, non-linearly, or along a curved path, from one end of the tendon or from one bone block to the other. The present application is additionally directed to bone tendon (BT) or bone tendon bone (BTB) grafts where a natural attachment between the tendon and the bone block(s) or bone portion(s) is maintained for at least a portion of the length of the bone block(s) or bone portion(s); or where a natural attachment between the tendon and the bone block(s) or bone portion(s) is maintained for the full length of the bone block(s) or bone portion(s).

When referring to bone tendon (BT) grafts, reference is often made to the Achilles Tendon as a common BT graft, with a bone block from the calcaneous or heel bone at one end and a free tendon or so called fan of tendon tissue separated from the soleus gastrocnemius, also referred to as the gastroc-soleus muscle group, or simply the calf muscle. When referring to bone tendon bone (BTB) grafts, reference is often made to the patellar tendon BTB, which includes the patellar tendon with a patellar bone block on one end and a tibial bone block on the other end. A BT graft may also be created by removing one bone block from a BTB graft. A BTB graft may also be created by assembling or attaching a natural or artificial bone block either to one end of a BT graft with a naturally attached bone block on the other end, or to one or both ends of a free tendon without any naturally attached bone block. In certain aspects, the present application is further directed to a tendon which is wider than a bone block assembled to one or both ends of a tendon with a non-anatomical attachment, where the tendon is wider than the bone block or bone blocks an configured to wrap around at least a portion of the bone prior to implantation.

The present application is further directed to an allograft bone tendon graft for use in orthopedic surgery in humans comprising a bone block attached to a tendon and having a natural attachment between the tendon and the bone block maintained along a first side of the bone block, and having at least one additional opposing side. The tendon comprises at least one section having a width greater than the width of the bone block; where the tendon width is sufficient to wrap around at least a portion of the opposing side and further where the bone block is preshaped for implantation in a bone tunnel during surgery.

The present application is further directed to allograft bone tendon (BT) or bone tendon bone (BTB) grafts where the tendon comprises a patellar tendon, quadriceps tendon or Achilles tendon. While the present application discusses many features of natural human or animal anatomy, it is understood that the invention claimed here encompasses non-anatomical features created from or in concert with, and in some cases making specific use of or in specified relation to, these anatomical features.

DETAILED DESCRIPTION

Figure 1:
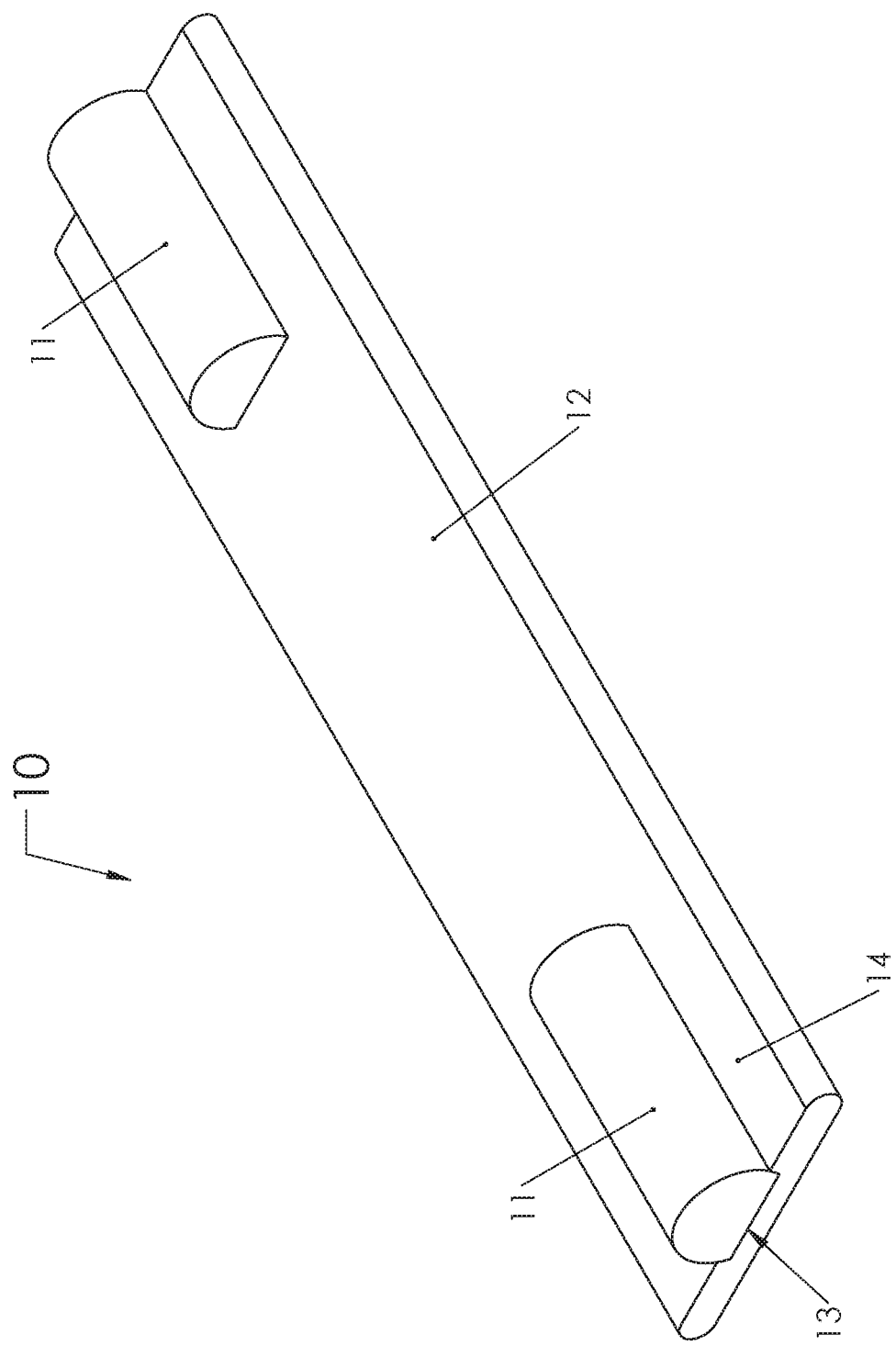
FIG. 1 shows an exemplary bone tendon bone graft of the application.

In the field of orthopedic medicine, there is a need to replace or correct bone, ligament and tendon defects or injuries. In cases such as Anterior Cruciate Ligament (ACL) or Posterior Cruciate Ligament (PCL) ruptures or tears, if the tendon rupture cannot be surgically reconnected or is unlikely to heal, a bone tendon or bone tendon bone graft is often used. Said grafts (or implants) can come from the patient themselves (autograft), from human cadaveric donors (allograft) or from other sources such as animal tissue (xenograft) or synthetic materials. Autograft, allograft or xenograft implants may advantageously act as a scaffold and be remodeled by the recipient's body over time such that autogenous bone and tendon tissue replaces the implant. Good remodeling can occur when autograft materials are used, but this is not always the best option for the patient. Use of autograft material requires a second surgery (to recover the graft from the patient), and greatly increases surgery time and possible complications from the second site of morbidity. Additionally, for some patients, autograft is not a possibility due to prior surgery, injury or anatomical deficiency.

Creation of surgical implants from natural tissues can mitigate the problems with autograft implants, while still allowing for effective grafts. When properly prepared to remove any deleterious material from the tissue, allograft or xenograft tissue can be a very effective tendon replacement graft material. Allograft or xenograft can remodel in the patient and be reincorporated and converted to host tissue during the healing process.

In certain embodiments the implant is an allograft, autograft or xenograft implant useful in surgery on an animal or on animals. In some embodiments the animal is a human or the animals are humans. In some instances allograft material is recovered from a human cadaver. In some instances autograft material is recovered from a human. In some instances xenograft material is recovered from a pig, a cow, a sheep, or other animal. In veterinary applications, it is contemplated that autograft, allograft or xenograft material is recovered from, useful in surgery on, and implanted into known species of animals including without limitation cats, dogs, cows, pigs, sheep, horses and other wild, domestic or agricultural animals.

Unshaped, natural or crudely shaped, bone-tendon and bone-tendon-bone tissue grafts can be used in surgical procedures. However, these grafts must be prepared for implantation into the patient during surgery, which requires excess operating room time. Unshaped bone-tendon-bone grafts must be specifically shaped for the recipient during surgery, which, in some cases, can require thirty minutes to over an hour of additional time. Thus, in one aspect, the application is directed to improved surgical implants made from tissue that have certain preshaped features that allow for more efficacious orthopedic surgery in humans. Such grafts are used to repair orthopedic injuries, e.g. Anterior Cruciate Ligament (ACL) or Posterior Cruciate Ligament (PCL) ruptures or tears, with reduced operating room time and greater ease for the surgeon.

Preshaping of the bone and tendon of allograft or xenograft materials allows for ease of use. Graft materials can be machined into preshaped forms that exactly match the surgical procedure. The surgeon then does not have to take valuable operating room time to shape the graft for implantation. Utilizing a preshaped graft reduces the overall time of the surgery and also the amount of time a patient is under anesthesia. Use of allograft can also reduce postoperative pain.

Preshaping allows for graft pre-processing and standardization and allows doctors to order the exact size they need for a given patient. Such implants are then processed, cleaned/passivated and placed in a sterile package. Assignee's U.S. Pat. Nos. 6,497,726; 8,007,533; 7,776,089; 8,470,038; 8,167,943; 7,727,278; 8,105,379; and 8,110,001 describe other preshaped allografts for orthopedic surgery; all of which are incorporated herein by reference in their entirety. In one aspect the present application is directed to surgical implants made from tissue that is machined into a preshaped form (from crude starting materials).

Applicants have determined that for preshaped bone tendon or bone tendon bone grafts additional advantages are afforded when the tendon that is wider than the bone blocks. This wide tendon allows for more collagen to be present at the site of implantation (bone tunnel), in some instances allowing for greater surface contact area between tendon graft and patient bone while still providing the strength of a natural bone to tendon attachment within the graft to facilitate fixation of the graft in the bone tunnel. This causes an increase in healing/remodeling in the patient. Without wishing to be bound by theory, it is presumed that the additional collagen provided by the wide tendon assists tendon to bone healing. The use of the wide tendon results in a stronger attachment of tendon to bone since it will have a bigger tendon footprint and bone-tendon healing interface due to the increased tendon collagen at the site of implantation.

When using bone tendon or bone tendon bone grafts in a patient, healing requires the graft to remodel and create a new tendon to bone interface (incorporating donor bone into the host bone). Tendon-to-bone healing can be slow due to the two inhomogeneous tissues (bone/tendon) thus it is advantageous to augment tendon to bone healing. Sharpey's fibers—strong collagenous fibers that connect to bone—are a part of the healing process between tendon and bone. After creation of a bone tunnel in a patient and insertion of a graft, formation of Sharpey's fibers can be an indicator of healing (indirect) between the tendon and bone. Applicants propose that Sharpey's fiber formation is increased in the presence of additional collagen at the bone tendon interface site (in the tunnel). The additional collagen, compared to known BT or BTB implants, is provided from the tendon portion that is wider than the bone portion of the graft, and the positive effect of this additional collagen on bone to tendon healing is thought to be further enhanced by the additional tendon to bone contact area afforded in certain embodiments.

Bone tendon (BT) or bone tendon bone (BTB) grafts are usually made in one of two ways: (1) by harvesting a naturally occurring tendon/ligament and portions of the bone(s) to which it is attached, thus maintaining the naturally occurring attachment of tendon/ligament and bone; or (2) by attaching the opposing ends of one or more pieces of tendon, ligament or a synthetic material to separate bone blocks. The name BTB is used for historical reasons. One skilled in the art recognizes that by definition, a "tendon" is a collagenous cord that attaches muscle to its point of origin, typically to bone. By definition, a "ligament" is a band of collagenous tissue that connects bone or supports viscera. Thus, it would appear that a BTB would more properly be called a bone-ligament-bone implant. However, many of the earliest BTBs employed a tendon, which is typically larger and generally more plentiful in a body. Hence, the name BTB became adopted by the art. We have used the term BTB to encompass all of the bone-soft tissue grafts described herein. The terms BT or BTB may also be used to refer to assembled bone-tendon grafts where one or more non-naturally-attached bone blocks is assembled at one or more locations along a natural or synthetic tendon scaffold.

In creating allografts (i.e. graft materials taken from a human donor cadaver), tendons that can be used in the present application include but are not limited to the patellar tendon, quadriceps tendon or Achilles tendon. Other tendons can be contemplated. At least one point of natural insertion between the bone and the tendon is maintained, which gives the graft stability and allows for greater healing. For allografts, in certain embodiments, the following bone-tendon pairs are utilized patellar bone and patellar tendon, a patellar bone and quadriceps tendon, a tibial bone and patellar tendon, and/or calcaneus bone and Achilles tendon.

The terms "graft" and "implant" can be used to refer to materials for implantation in a human. The terms "graft" and "implant" are used interchangeably herein. "Implant" (or "graft"), as used herein, refers to any material the implantation of which into a human or an animal is considered to be beneficial. Accordingly, the implant may be tissue-derived material, such as bone, skin, and the like, or it may be a metallic or synthetic material having an external surface or internal structure that may require cleaning, sterilization or passivation. An implant may comprise autograft tissue, allograft tissue, xenograft tissue or combinations thereof, and in the case of mineralized tissues, such as bone, the implant may comprise mineralized tissue, partially demineralized tissue, completely demineralized tissue, and combinations thereof.

Allograft materials require recovery, treatment and preparation for implantation. In order to be suitable for implantation in humans, allograft or xenograft implants are often treated to remove antigenic proteins, which may generate rejection of the implant. The graft also may be treated to remove bacteria, viruses, spores, etc. Use of the assignees' patented method for passivating tissue results in grafts that have at least about a 5 to 6 log reduction in any form of viable organisms (viruses, bacteria, amoebae, rickettsia, fungi). This method also has the added benefit of removing blood, cellular debris, and soluble and antigenic proteins. The method subjects the implant to alternating cycles of pressure and vacuum in the sequential presence of solvents/cleaning agents, such as isopropyl alcohol, hydrogen peroxide and a detergent. These solvents/cleaning agents perfuse the tissue and passivate it. These processes are disclosed in full detail in assignee's U.S. Pat. Nos. 6,613,278; 6,482,584; 6,652,818; 8,669,043; 8,142,991; 6,613278; 9,332,750; and 7,648,676; all of which are incorporated herein by reference in their entirety. The process results in a final implant that is able to be placed in sterile packaging and delivered for implantation.

As used herein, the term "passivate" is intended to refer to the elimination of potentially pathogenic organisms and immunogenic substances from an implant. Thus, both sterility and reduced antigenicity is intended by this term, although elimination of beneficial biological properties of the implant, such as osteogenic properties (osteoconduction or osteoinduction; bone fusion), natural tissue functionality, and desirable structural strength of an implant are not intended by this term. The term "passivation" is preferred to the term "sterilize" because, while sterilization is a goal, that term has an absolute connotation for which the ability to definitively test is limited by the state of the art of making such measurements and/or by the need for attendant tissue destruction. In addition, while the implants produced according to the method of this application may not be completely devoid of any antigenicity or pyrogenicity, these undesirable aspects are greatly reduced, and this too is intended by the term "passivation," as used herein.

Grafts that have been passivated can be placed in sterile packaging and stored until time of surgery. Surgeons can order the size of graft that is desired for the patient. Thus grafts are ready "off the shelf" which drastically cuts down on preparation and overall operation time.

When bone tendon bone or bone tendon grafts are passivated, it is contemplated to use tensioning or kinematic restraint of the tissue. This avoids problems with tissue having different exposures to the cleaning agents (for example, as a result of overlapping tissues or tissues wrapped around themselves) or shriveling or other changes to the tissue. By applying tension to an implant comprising a soft tissue during a treatment process employing cleaning agents, the positioning of the soft tissue in a treatment chamber can be maintained in a desired fashion, and the cleaning agents are unlikely to be applied with enough force to change the positioning. Because cleaning agents contact the implants (particularly the soft tissue) more uniformly and predictably, there will be more consistency between different implants and within a single implant. Soft tissues will have fewer tendencies to shrivel, and as a result there will be less likelihood of generating implants having undesirable appearance or structural changes. By applying tension to a soft tissue during a treatment process, inflammation and damage from swelling reactions (e.g. foaming) within the tissue during treatment can be reduced, because there is greater opportunity for the foaming action to exit the stretched tissue, rather than remain inside the tissue to cause more damage. Additionally, the tension applied during processing will protect the graft from post-surgical laxity which can be caused by shrinkage and shriveling of the graft during conventional processing.

The terms "perfused" or "perfusion," as used herein, are intended to imply efficient interpenetration of cleaning solutions into and through the channels and crevices of materials intended for implantation into a recipient. As used herein, the terms "rapid" or "rapidly" as they are applied to the process of pressure cycling according to this application mean time frames on the order of seconds to minutes, rather than hours or days. The terms "sonicate" or "sonication" as used herein means the application of sonic or ultrasonic energy via a container of an implant undergoing processing according to the method of this application under conditions that permit efficient transfer of the sonic energy to the implant. Also called ultrasonic bombardment. Sonic energy may be transferred through a fluid to a workpiece such that efficient cleaning and bacterial or cellular disruption is achieved, without resulting in gross structural damage to the workpiece.

"Soft tissue", as used herein, refers to any biological tissue other than bone, including but not limited to tendons, ligaments, fascia, whole joints, dura, skin, pericardia, heart valves, veins, neural tissue, submucosal tissue (e.g. intestinal tissue), and cartilage. The "soft tissue" described herein is typically a collagenous material that is autograft, allograft or xenograft. The soft tissue can be a predetermined length of tendon, a bundle of tendons of the same or different lengths, a predetermined length of ligament, a bundle of ligaments of the same length or different lengths, a segment or segments of pericardium, dermis, fascia, dura, skin, submucosal tissue (e.g., intestinal tissue), cartilage, or a combination thereof. In one embodiment, the source of the soft tissue is a tendon.

Crude bone tendon or bone tendon bone grafts are recovered from a donor cadaver (human or other animal). These crude grafts contain natural attachments between the donor bone and tendon. When creating preshaped grafts, the natural attachment between the tendon and the bone is maintained along at least one side of the bone block or portion. In certain aspects, the widths of the bone blocks of the crude grafts are between about 20 to 50 mm wide, alternatively between about 10 to 75 mm wide, alternatively between about 15 to 30 mm wide. In the crude bone blocks, the tendon typically covers the entire width of the bone block. Crude grafts may often be defined by rough or straight cut edges where they are excised from the donor cadaver. Crude grafts may also be defined as those having a shape not suitable for implantation into a bone tunnel at the implant site, such as a whole or hemi patellar tendon with bone blocks or a whole or hemi Achilles tendon with calcaneous bone block.

Preshaped bone tendon or bone tendon bone grafts are similarly recovered from a donor cadaver (human or other animal). These preshaped grafts contain natural attachments between the donor bone and tendon which are maintained along at least one side of the bone block or portion. Preshaped grafts may be defined as those having a shape suitable for direct implantation into a bone tunnel in the leg of a recipient or patient. In certain aspects, the widths of the bone blocks of the crude grafts are between about 5 to 20 mm wide, alternatively between about 6 to 16 mm wide, alternatively between about 7 to 14 mm wide, alternatively between about 9 to 14 mm wide, alternatively any of about 8, 9, 9.5, 10, 10.5, 11, 12, 13, 14, or 15 mm wide. This width may describe a measurement across two flat surfaces, between two opposing edges or surfaces, between two opposing points, across a diameter or effective diameter, or across two opposing sides or surfaces of a cylinder or other shaped bone block. This width may also describe a measurement achieved by passing the bone block through or comparing against a sizing gauge or aperture or artifact.

FIG. 1 shows an embodiment of the present application. A wide bone tendon bone (BTB) graft 10 is shown having two preshaped bone blocks 11 and a tendon 12 which is wider than the bone blocks. The natural interface between bone and tendon is maintained along the back side of the bone block at interface 13. Tendon "wings" 14 are shown alongside the bone block. These widths of tendon ("wings") are derived from the tendon that was previously attached to the portion of the bone block that was machined away.

Referring to FIG. 1, the present application is directed to grafts 10 that have a bone block or portion 11 connected via a natural attachment to a tendon 12 through at least one interface 13. In one embodiment, the natural attachment between the tendon and the bone is maintained for the full length of the preshaped bone block/portion. In certain embodiments the width of the tendon is maintained substantially the same along the length of the implant. In certain other embodiments the width of the tendon is varied along the length of the implant. In some embodiments the width of the tendon is greater than that of the bone block in at least one region around one or both bone blocks, but less than the width of the tendon at one or more points or regions along the length between the bone blocks. In some embodiments the width of the tendon is greater than that of the bone block in at least one region around one or both bone blocks, and also greater than the width of the tendon at one or more points or regions along the length between the bone blocks. In certain embodiments, the tendon may also be left to extend in length beyond one or both bone blocks with a width that is the same, less than or greater than the adjacent bone block and also the same, less than or greater than the adjacent or distant regions or sections of the tendon.

The present application is directed to bone tendon bone (BTB) or bone tendon (BT) grafts having a tendon or tendon portion that at least in part, is wider than the bone block(s)/portions(s). In one embodiment, the tendon is from 1.1 to 5 times as wide as the bone. In another embodiment, the tendon is from 1.5 to 5 times as wide as the bone. In a further embodiment, the width of the tendon is at least 1.5 times the width of the bone. In other embodiments, the width of the tendon is about 1.1, 1.2, 1.3, 1.4, 1.5, 1.6, 1.7, 1.8, 1.9 or 2.0 times the width of the bone.

In some embodiments, the width of the bone block can be from about 8 mm to about 12 mm, alternatively from about 9 mm to about 11 mm. In certain embodiments, the width of the bone block is about 10 mm. In certain embodiments, the width of the wide tendon is about 9 mm to 60 mm. In certain embodiments, the width of the wide tendon is from about 9 mm to 40 mm.

Figure 2:
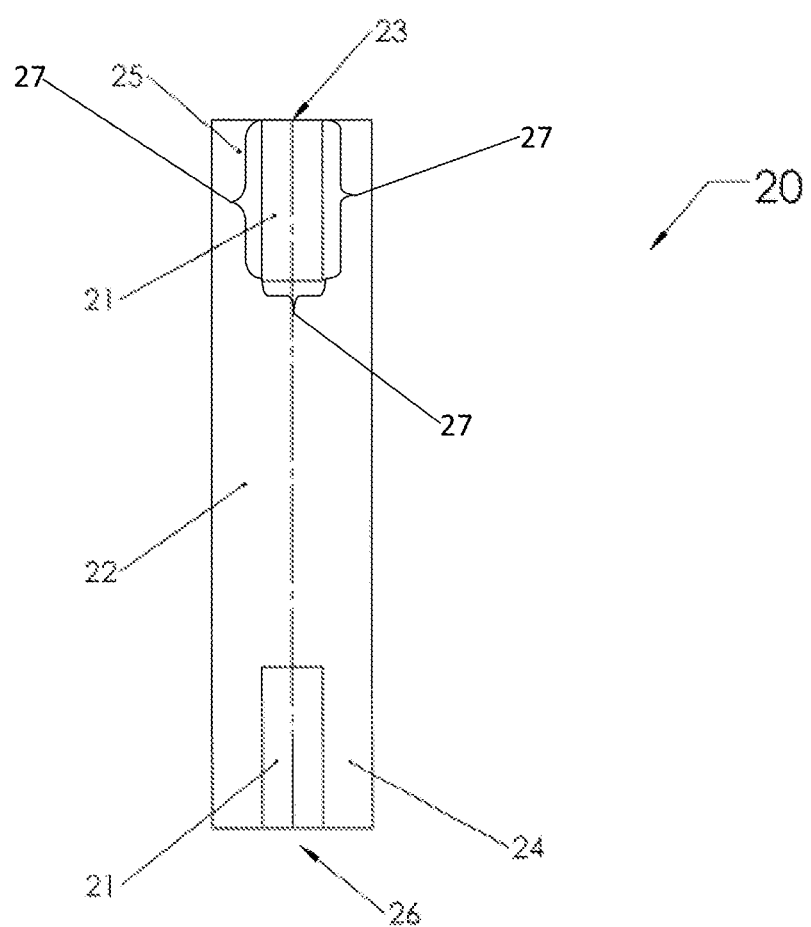
FIG. 2 shows a top down view of an exemplary bone tendon bone graft of the application.

FIG. 2 shows another view of an embodiment of the present application. A wide bone tendon bone (BTB) graft 20 is shown having two preshaped bone blocks 21 and a tendon wider than the bone blocks 22. The natural interface between bone and tendon is maintained along the back side of the bone block at interface 23 and at the cut sides and end (collectively 27) of the bone block 21. Tendon wings 24 are shown alongside the bone block. In one aspect, when the grafts of the application are used for surgery, the soft tissue (tendon) is wrapped or folded along this longitudinal axis. A dotted line 26 is shown to represent the longitudinal axis of the graft.

Figure 3:
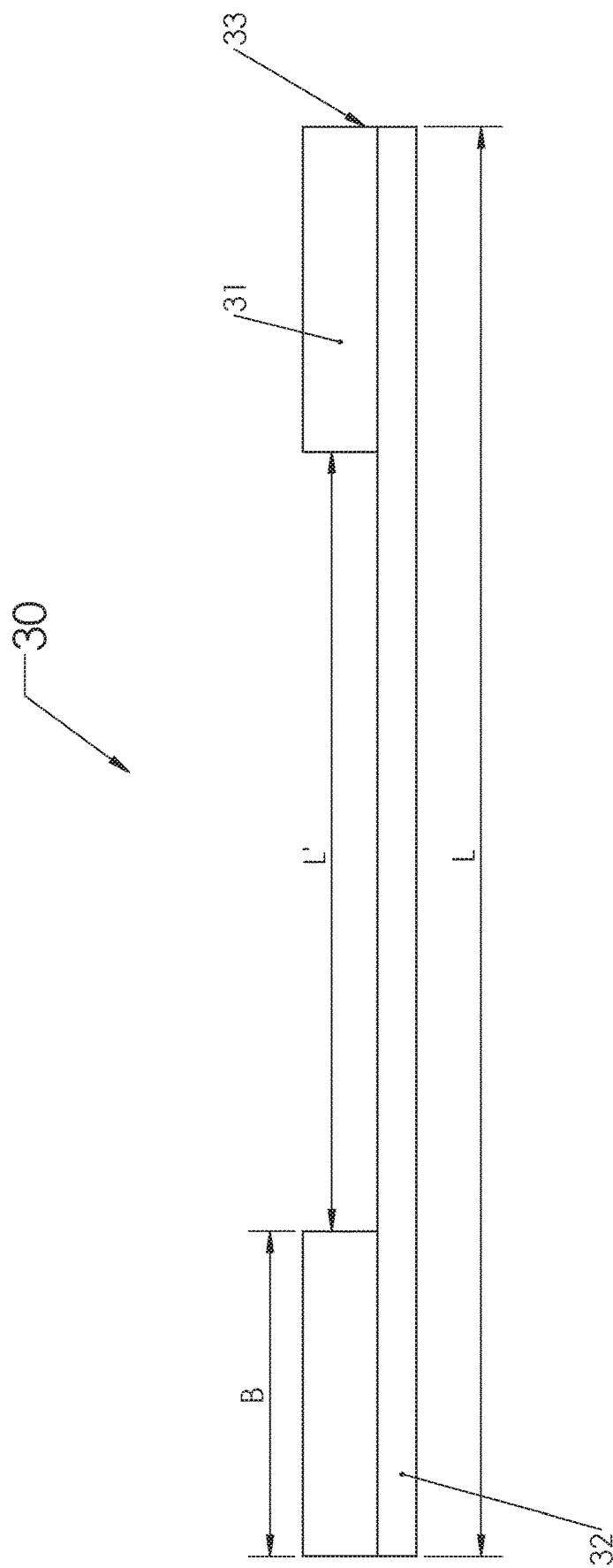
FIG. 3 shows a side view of an exemplary bone tendon bone graft of the application.

FIG. 3 shows a side view of an embodiment of the present application. A wide bone tendon bone (BTB) graft 30 is shown having two preshaped bone blocks 31 and a tendon 32. The natural interface between bone and tendon is maintained along one side of the bone block at interface 33. A length L is shown that corresponds to the entire length of the graft, from end to end. Another length L' is shown that corresponds to the length of the tendon between the bone blocks. The length of the bone block, B, is also defined.

The length of the whole graft, L, can be from about 60 m to about 200 mm. In certain embodiments, the length is about 60 mm to 145 mm. The length of the tendon between the bone blocks, sometimes referred to as the gauge length, L', is usually about 30 mm to about 100 mm, due to anatomical constraints. In certain embodiments, the length is about 30 mm to 75 mm. The length of the bone blocks, B, is typically about 10 to about 45 mm. In certain embodiments, the bone block length is about 15 mm to about 35 mm, alternatively about 20 mm to about 30 mm, alternatively about 23 mm to about 27 mm, alternatively about 25 mm.

Figure 4:
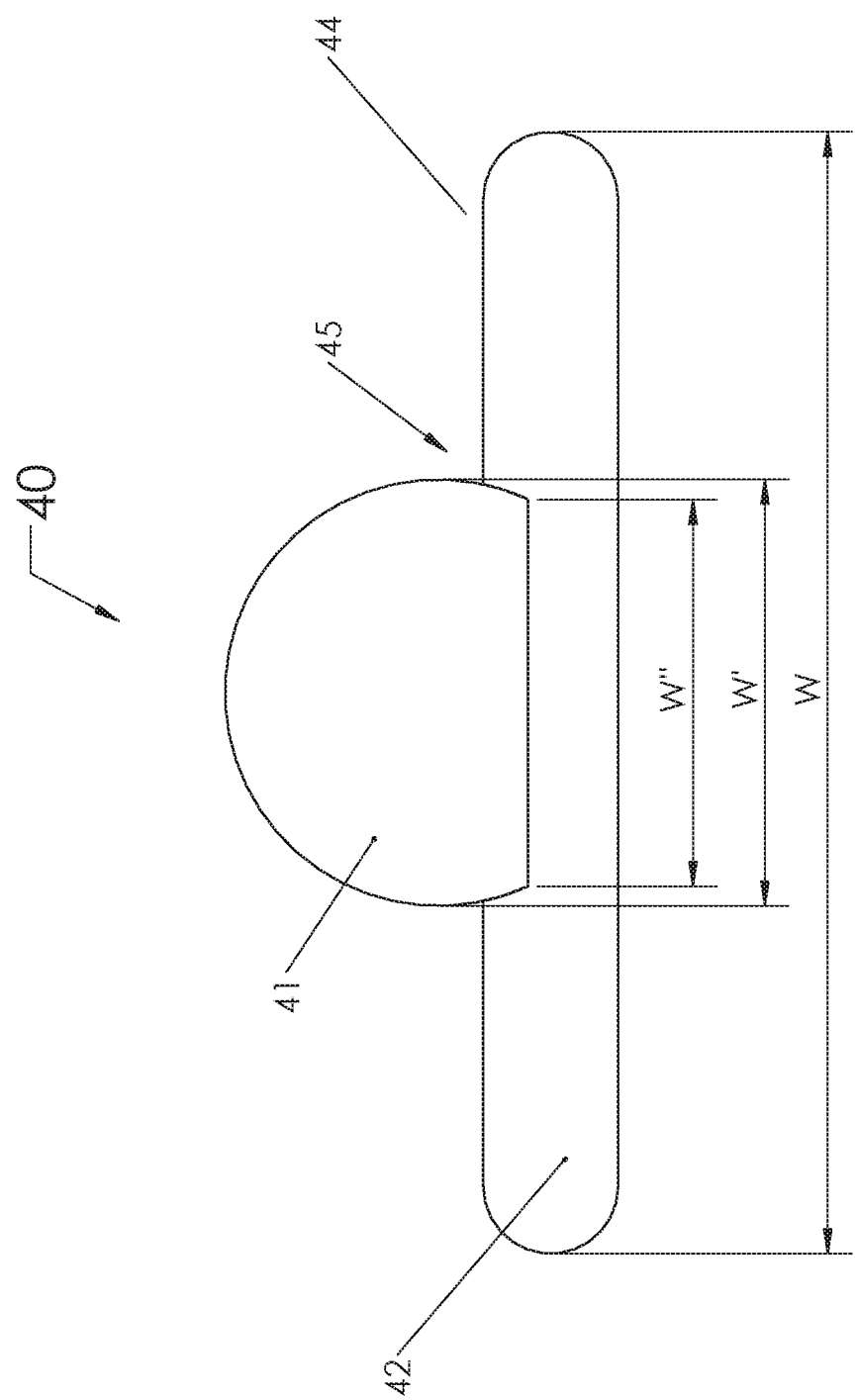
FIG. 4 shows an end on view of an exemplary bone tendon bone graft of the application.

The present application is directed in one aspect to grafts that have a bone block or portion that is preshaped to fit in a bone tunnel when used for orthopedic surgery. In one embodiment, the bone block or bone portion comprises a cross-sectional profile selected from the group consisting of semi-circular, semi-ovular, triangular, trapezoidal, rectangular, square, curvilinear, and combinations thereof. Other cross sections such as polygonal and elliptical are also contemplated. BT or BTB implants are also contemplated in certain aspects with bone blocks of a crude or non-preshaped nature but still having one or more tendon wings, resulting in a tendon wider than the bone block and in certain embodiments capable of wrapping around, surrounding or covering some portion or all of the bone block or one or more sides of the bone block either before, after, or in the absence of further shaping by the surgical team intraoperatively or preoperatively FIG. 4 shows an end on view of an exemplary bone tendon bone graft 40 of the application. The bone block 41 is shown; in this embodiment the bone block is semi-circular in cross section. The bone block 41 maintains the natural attachment 45 to the tendon 42. The tendon is wider than the bone block with "wings" 44 to the side of the bone block. A width W is shown across the tendon from edge to edge. Another width W' is shown across opposing faces of the bone block. Another width W" is shown across the endpoints of the bone block where it meets the tendon. It is seen that width of the bone block may be measured from two opposing sides of a cylindrical or other shape, from two available flat sides, edges or points, or from two endpoints, such as where the tendon meets the bone block. In certain embodiments the width of the bone block or of the tendon is measured from the widest point in the area being measured.

Figure 7:
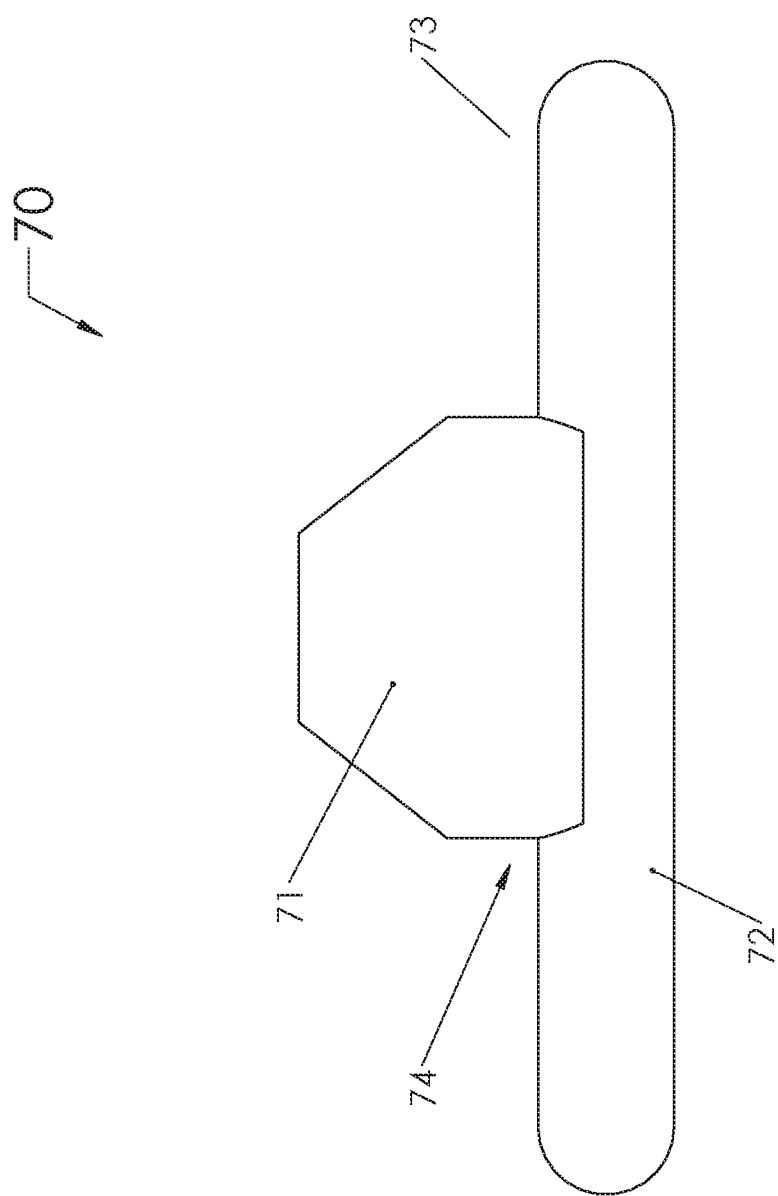
FIG. 7 shows an end on view of an exemplary bone tendon bone graft of the application.

FIG. 7 shows an end on view of another exemplary bone tendon bone graft 70 of the application. The bone block 71 is shown; in this embodiment the bone block is polygonal in cross section. The bone block 71 maintains the natural attachment 74 to the tendon 72. The tendon is wider than the bone block with "wings" 73 to the side of the bone block.

Figure 5:
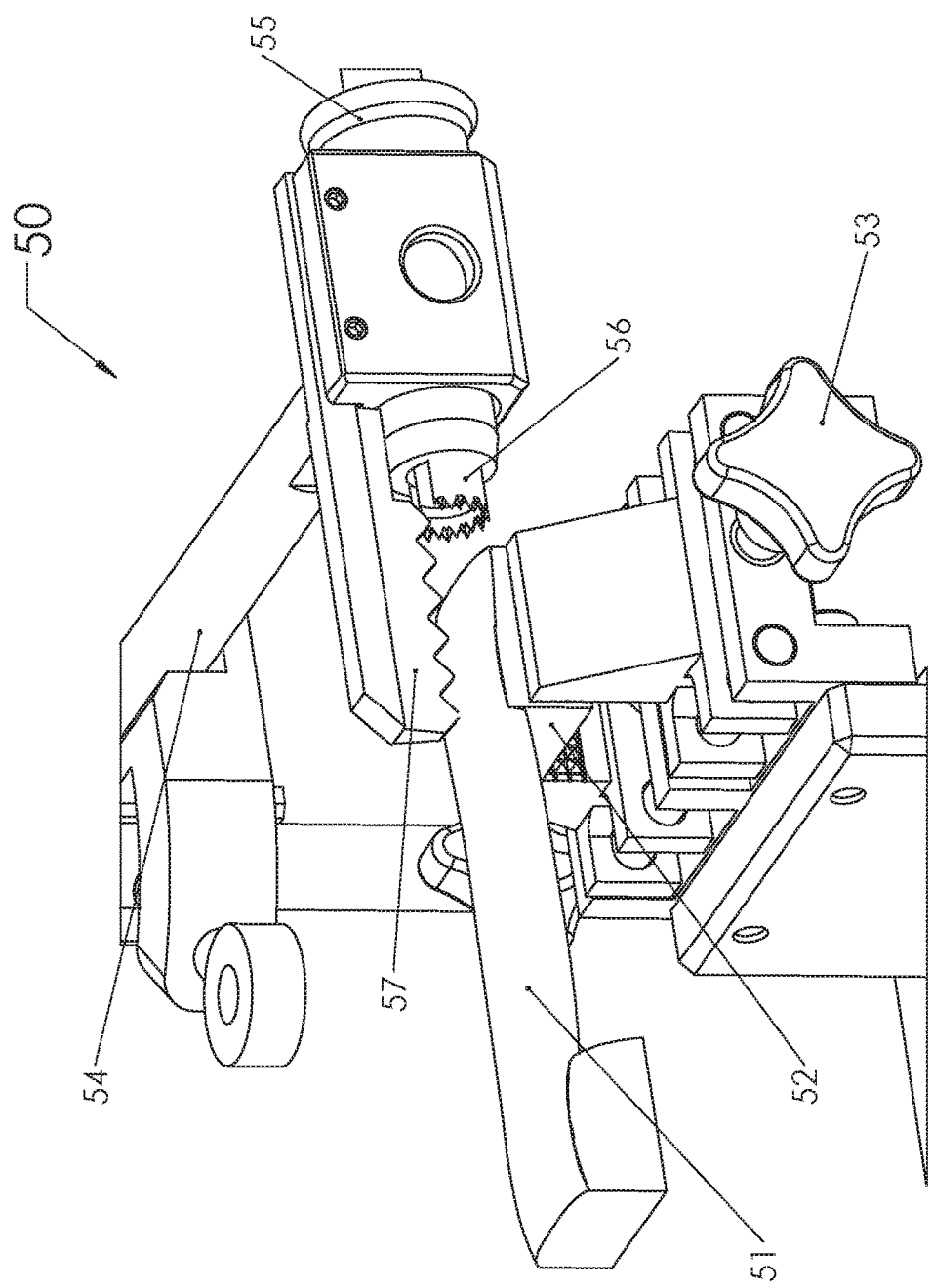
FIG. 5 shows one exemplary set up for making an exemplary bone tendon bone graft of the application.
Figure 8:
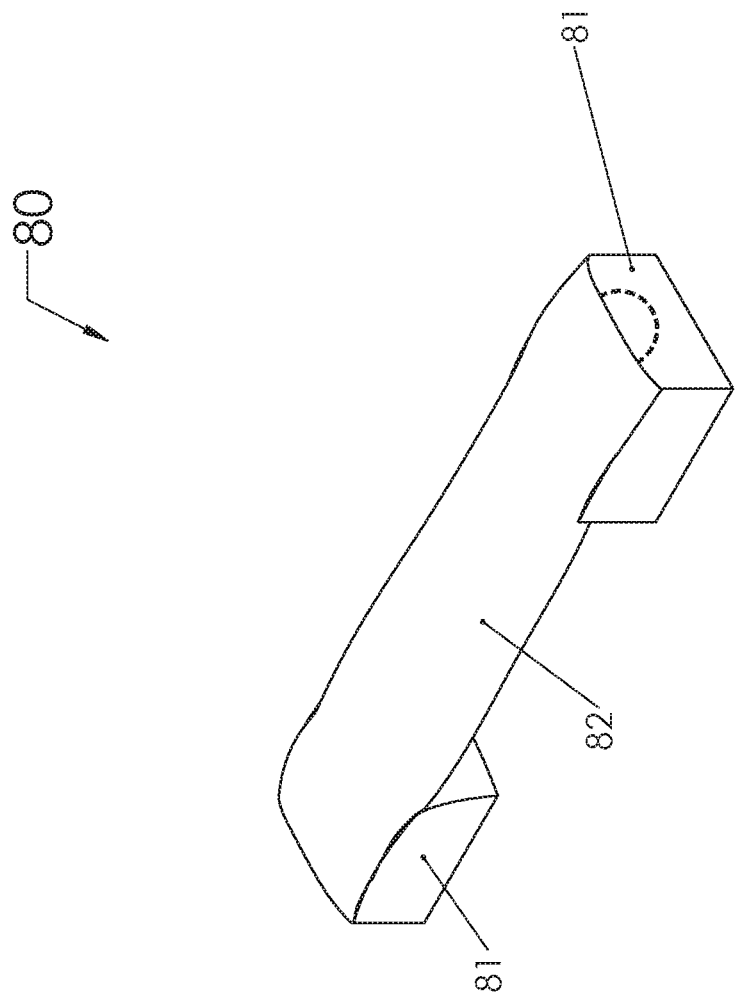
FIG. 8 shows a crude BTB graft that may be used as an exemplary starting material for making a bone tendon bone graft of the application.

FIGS. 5 and 8 show aspects of the crude starting material for making the grafts of the application (FIG. 8) and the apparatus used to machine the preshaped bone blocks (FIG. 5). FIG. 5 is a view of a vise/clamp set up 50 that can be used in the preparation of grafts. This is further discussed in the Example below. In one aspect, an oscillator/cutter 56 is used to machine the preshaped bone block from the crude bone block. The oscillator/cutter is used with a cutting path and an associated amplitude that does not cut through the tendon, but only the bone. The tooth pattern on the end of the oscillator/cutter is also chosen to be favorable for cutting through bone but not tendon. This allows for all or most of the original tendon from the crude starting material to be maintained as a tendon having "wings" (see FIG. 1, 14). In other words, in the final BT or BTB product, the tendon that remains after preshaping the bone block is wider than the bone block.

Figure 6:
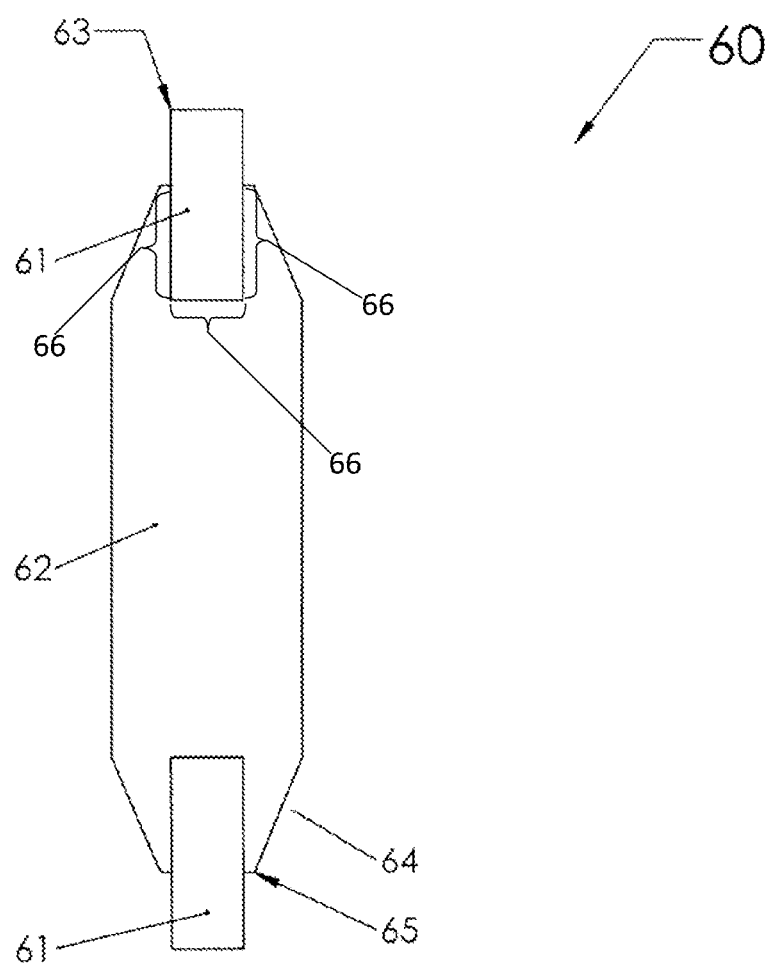
FIG. 6 shows a top down view of an exemplary bone tendon bone graft of the application.

FIG. 6 shows a top down view of another exemplary bone tendon bone graft of the application. In this embodiment, a wide bone tendon bone (BTB) graft 60 is shown having two preshaped bone blocks 61 and a tendon 62. The natural interface between bone and tendon is maintained along a portion of one side of the bone block passing through interface line 65. The natural interface between bone and tendon is maintained along the back side of the bone block at interface 23 and at the cut sides and end (collectively 66) of the bone block 61. In this embodiment, some of the wide tendon is trimmed away at the distal end of the bone block, creating an angled portion of the wide tendon 64. In other embodiments, the tendon can be trimmed away in a different shape, such as curved. In some embodiments the shaping of the tendon wing may be symmetrical, essentially symmetrical, asymmetrical, or varied from side to side and from one bone block to another. In these embodiments, the natural attachment between the tendon and the bone is typically maintained for a portion of the length of the bone. In some embodiments, the natural attachment is maintained for at least about 1/10th to at least about 3/4th of the preshaped bone block bone length. In some embodiments, the natural attachment is maintained for about 1/2 of the preshaped bone block bone length. In some embodiments, the natural attachment is maintained for substantially about all of the preshaped bone block bone length. In some embodiments, the full width of the tendon wing is maintained for at least about 1/10th to at least about 3/4th of the preshaped bone block bone length. In some embodiments, the full width of the tendon wing is maintained for about 1/2 of the preshaped bone block bone length. In some embodiments, the full width of the tendon wing is maintained for substantially about all of the preshaped bone block bone length. In some embodiments the natural attachment is maintained for the full length of the bone block while the width of the tendon wing or wings is varied along the length of the bone block. In some embodiments the tendon wings may be formed, cut or folded at one or more cross sections to create a feature such as a tab, pull, thickened section or extension.

In certain embodiments a similar or different shaped tendon wing may be achieved by folding over a portion of the tendon to reach the desired profile. Whether the tendon wing shape is achieved by cutting, folding, a combination of cutting and folding, or some other method, the preshaped bone block may be shaped to accommodate tendon material or tendon wing shape and support fixation in the bone tunnel. As a non-limiting example, in some instances the bone block may be recessed in the area around the tendon wing to allow space for the tendon tissue to wrap or fold into place and fit within the bone tunnel with a desired amount of compression or a desired amount of tissue overlap.

In some embodiments one or more regions of the tendon may be designed to compress not at all, or as much as about 10%, about 20%, about 30%, about 40%, about 50% or more after wrapping around the bone block and insertion into the tunnel but prior to fixation of the implant in the tunnel. In some embodiments the tendon may leave essentially none, or as much as about 5%, about 10%, about 20%, about 30%, about 40%, about 50%, about 60%, about 70%, about 80%, about 90%, about 95% or more of the bone block exposed after wrapping of the tendon wing or wings around one or more sides of the bone block.

In some embodiments the cross sectional area or height of the bone block may be reduced by removal, crushing or compressing of bone material in one or more regions by about 5%, about 10%, about 20%, about 30%, about 40%, about 50%, about 60%, about 70%, about 80%, about 90%, about 95% or more to allow space for the wrapping of the tendon wing or wings around one or more sides of the bone block. In some embodiments the reduction in cross sectional area or height of the bone block may occur along about 5%, about 10%, about 20%, about 30%, about 40%, about 50%, about 60%, about 70%, about 80%, about 90%, about 95% or more of the length of the bone block to allow space for the wrapping of the tendon wing or wings around one or more sides of the bone block.

In certain embodiments, one or more sections of the bone block may be reduced in height or cross sectional area down essentially to the level of the cortical bone cap where the tendon attachment occurs, alternatively to within about 0.5 mm of the tendon attachment, alternatively to within about 1 mm of the tendon attachment, alternatively to within about 2 mm of the tendon attachment, alternatively to within about 3 mm of the tendon attachment, alternatively to within about 4 mm of the tendon attachment, alternatively to within about 5 mm of the tendon attachment, alternatively to within about 6 mm of the tendon attachment, alternatively to within about 7 mm of the tendon attachment, alternatively to within about 8 mm of the tendon attachment, alternatively to within about 9 mm of the tendon attachment, alternatively to within about 10 mm of the tendon attachment, In certain embodiments the preshaped bone block may be reduced proportionally along a portion of its length, resulting in a wedge or tapered shaped bone block. In certain embodiments the preshaped bone block may be reduced a fixed amount along a portion of its length, resulting in a stepped bone block. In certain embodiments the preshaped bone block may be reduced from the proximal end of the bone block, nearest the mid-substance of the tendon. In certain embodiments the preshaped bone block may be reduced from the distal end of the bone block, opposite the mid-substance of the tendon.

FIG. 8 shows a crude bone tendon bone graft 80 that can be a starting material for preparation of grafts of the application. The crude BTB graft has a wide tendon 82 and two bone blocks 81. A dotted line shows the outline of one potential preshaped, machined bone block that can be created from this starting material.

Figure 9:
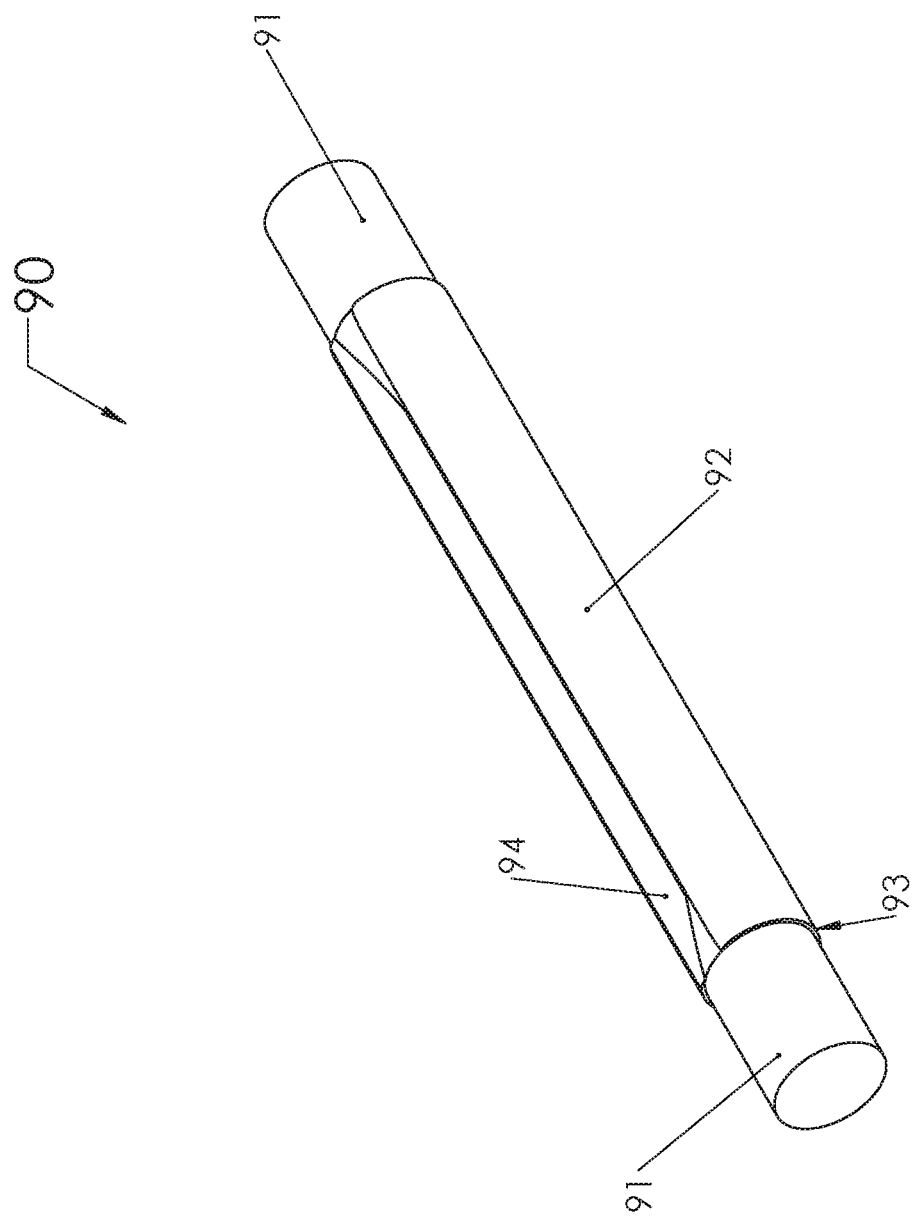
FIG. 9 shows a view of an exemplary embodiment of a rolled or folded bone tendon bone graft of the application.

There are a variety of configurations that are contemplated when using the grafts of the application in a surgery, such as wrapping, folding, rolling or "tubularizing" (i.e. rolling the wide tendon in such a way as to make a tube-like form). See FIGS. 9 and 10. This can be done immediately before implantation in the patient, or in advance of surgery. In one aspect, the rolled or folded graft can be sutured to hold the rolled soft tissue in place. Note that in some instances the tendon wraps around sides of bone block, not the ends of the bone block. In other instances the tendon may wrap around the end or ends of the bone block, or the tendon may wrap around both one or more sides and one or more ends of the bone block FIG. 9 shows a view of an embodiment of where the wide tendon is rolled or folded into a construct for implantation. FIG. 9 shows a view of a "tubularized" graft of the application 90. This graft has the tendon 92 folded or rolled inward around the bone blocks 91 to create a tube-like shape. In this embodiment, the tendon bone interface 93, (at the wing, or wide portion of the tendon) occurs part of the way down the bone block. In other embodiments, the interface can start at either end of the bone block, e.g. the interface can run the length of the bone block, or be present for at least part of the length of the bone block. In other words, the width of the tendon can be maintained for its full length, or the width of said tendon can be maintained for part of its length. In certain aspects, the width of the tendon can be maintained for least half its length. The wings of the tendon, when folded or rolled, can meet, or almost meet, at the top of the graft as shown 94.

Figure 10:
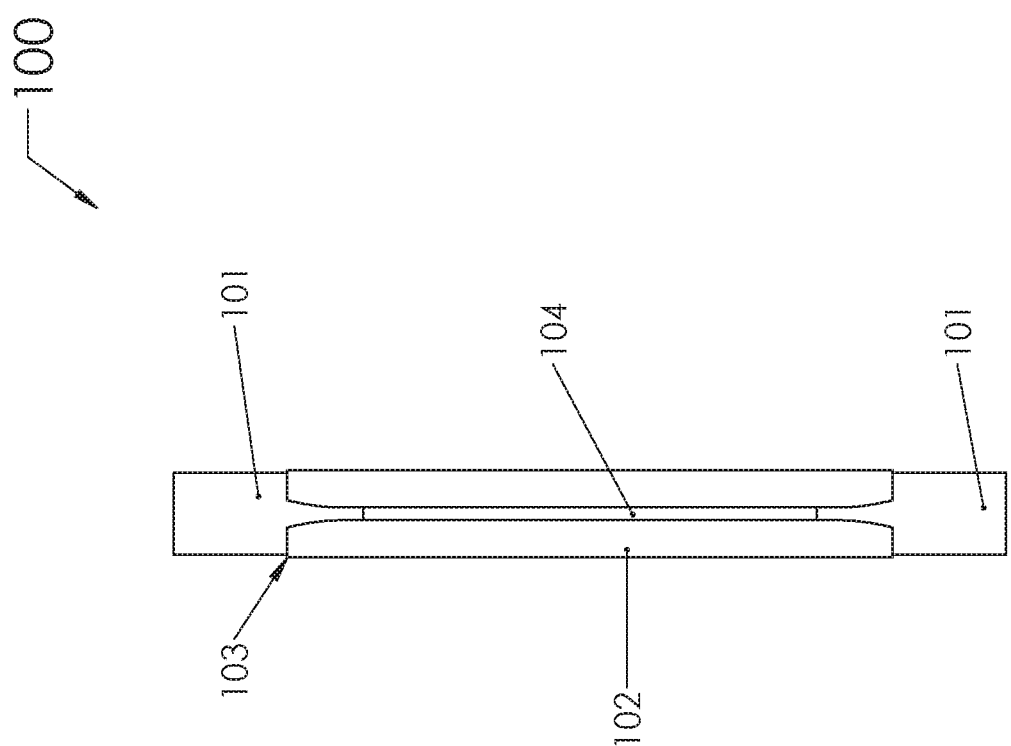
FIG. 10 shows a top down view of an exemplary embodiment of a rolled or folded bone tendon bone graft of the application.

FIG. 10 shows a top down view of an embodiment of where the wide tendon is rolled or folded into a construct for implantation. FIG. 10 shows a view of a "tubularized" graft of the application 100. This graft has the tendon 102 folded or rolled inward around the bone blocks 101 to create a tube-like shape. In this embodiment, the tendon bone interface 103, (at the wing, or wide portion of the tendon) occurs part of the way down the bone block. In other embodiments, the interface can start at either end of the bone block, e.g. the interface can run the length of the bone block, or be present for at least part of the length of the bone block. In other words, the width of the tendon can be maintained for its full length, or the width of said tendon can be maintained for part of its length. In certain aspects, the width of the tendon can be maintained for least half its length. The wings of the tendon, when folded or rolled, can meet, or almost meet, at the top of the graft as shown 104.

The present application is further directed to implants or grafts where the bone block or bone portion comprises a further preshaped feature created to accommodate the tendon or tendon portion when wrapped around for placement of said implant into a human patient. Bone blocks can be preshaped in a way that allows more of the "tubularized" tendon to fit into the tunnel in the patient. In other words, the bone block can be cut out in such a way to create a recess that the wrapped tendon fits in. In some aspects, the use of a wider tendon (especially when rolled or folded) means that less bone can be used, since the diameter of the tunnel in the patient is often fixed. In converse, as the tendon becomes narrower, bone volume can increase.

Figure 11:
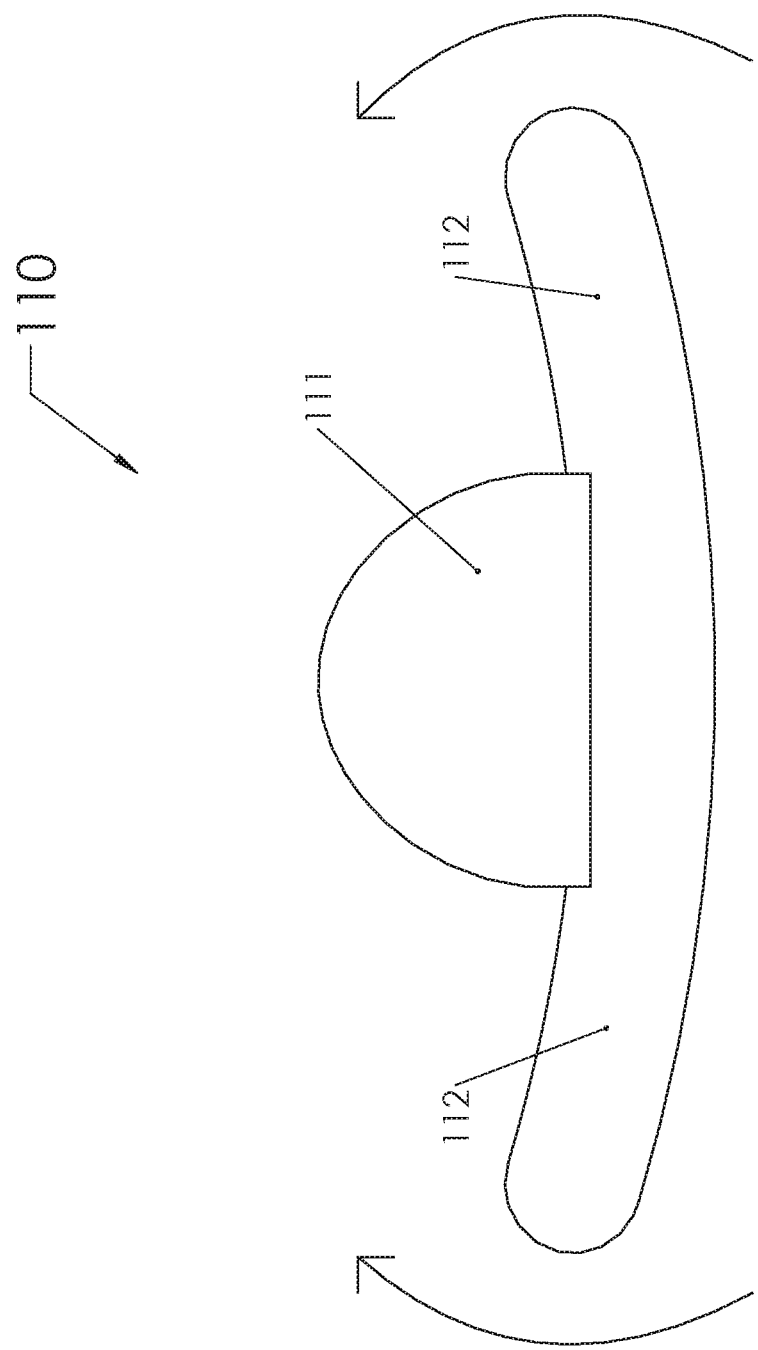
FIG. 11 shows an end on view of an exemplary bone tendon bone graft of the application. The tendon "wings" are being folded or rolled in the direction of the arrows.

FIG. 11 shows an end on view of another exemplary bone tendon bone graft 110 of the application. The tendon "wings" 112 are being wrapped or rolled in the direction of the arrows. Wrapping of the tendon occurs down the length of the graft and involves folding the two tendon portions that flank the bone block ("wings") in towards the centerline of the graft. The centerline (i.e. longitudinal axis) of the graft is shown in FIG. 2, 26.

In other aspects, the bone block or bone portion comprises a further preshaped feature created to aid in placement or fixation of the graft. Non-limiting examples of such features would be a groove for an interference screw or a hole for a cross pin. In further aspects, the bone block or bone portion comprises a tapered section. Such tapered sections can be arranged to accommodate rolled tendon or be created to aid in placement of the graft in the tunnel.

Figure 12:
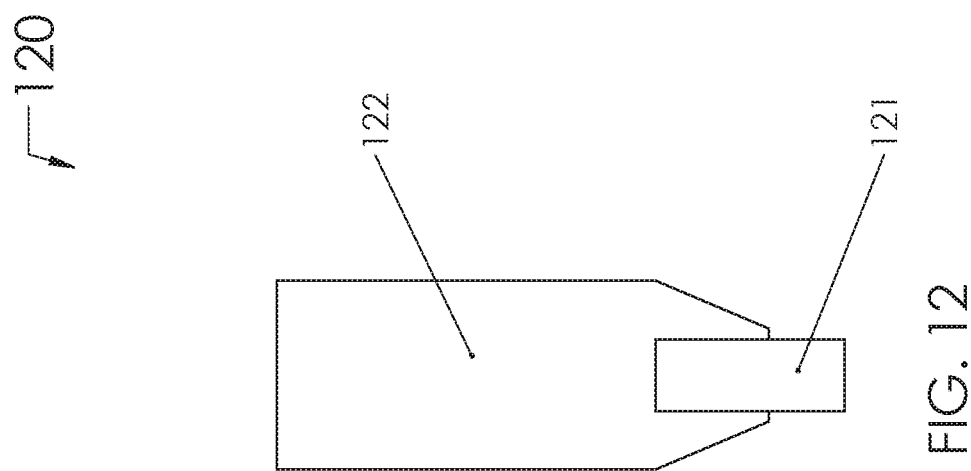
FIG. 12 shows an exemplary embodiment of a bone tendon graft of the application.

Grafts having a bone block on only one end are also contemplated. FIG. 12 shows one embodiment of such a graft. The bone tendon graft 120 has a tendon 122 and a preshaped bone block 121. In some embodiments, the other end of the bone tendon graft is free tendon. It is also contemplated that a bone block could be added to the free tendon end by assembling pieces that grip the tendon, or a bone block could be sutured to the tendon.

Figure 13:
FIG. 13 shows a photograph of a top down view of an exemplary bone tendon bone graft of the application
Figure 14:
FIG. 14 shows a photograph of the bottom side of the graft shown in FIG. 13.

FIGS. 13 and 14 show photographs of individual grafts that are made by certain methods of this disclosure. Note the tendon is much wider than the bone block and that the bone block remains attached to the tendon via a natural attachment along the back side. FIG. 13 shows the graft from the top and FIG. 14 shows the same graft, flipped over, thus showing the bottom of the graft and the natural tendon-bone attachment.

One aspect of the present application is providing improved grafts useful for orthopedic surgery such as ACL replacement. Such surgery is performed after injury (e.g. tear or rupture) in order to restore functional stability to the joint (knee). This surgery is usually performed arthroscopically. Small incisions (portals) are made in the knee and surgical instruments are inserted through these portals. A drill is inserted through the portal and tunnels are drilled through the tibial plateau or proximal tibia and femoral condyle at the knee joint. The graft is inserted through the tunnels and is fixed in place using various methods, such as fixation screws (interference screws).

In certain embodiments, a hole (not shown) can be placed through the bone block and used to accept suture during surgery for purposes of holding, guiding, or pulling graft into place in the bone tunnel and for tensioning the graft prior to and during fixation. Additional relief or guidance features such as slots, ridges, or small grooves (not shown) allow the suture to be routed away from other fixation elements such as interference screws and thus protected from damage or cutting of the suture during fixation, thus ensuring the ability to hold tension on the graft during implantation

EXAMPLE

In one non-limiting exemplary embodiment, a preshaped allograft bone tendon bone graft (BTB) having at least a portion of the tendon that is wider than the bone blocks is made by the following method. For a bone tendon bone graft, each bone block is cut separately.

The crude BTB bone block or Achilles bone block is prepared by cutting off the outer edges of the bone parallel to the tendon fibers. A vise/clamp set up 54 is used to hold the crude graft for machining the bone block; see FIG. 5. Width of the crude graft is less than 30 mm to fit the opening of the vise. A PEEK bushing 55 is inserted into the fixture. One crude bone block 52 is secured in the vise as shown in FIG. 5, using screw 53 to tighten the crude bone block in the vise.

The bone block is secured with about ⅓ of the bone block protruding above the vise and the back edge in line with the edge of the vise. The tendon/bone interface is maintained horizontal and parallel to the top of the vise (see FIG. 5; 51 (tendon) and 52 (crude bone block)). Next, the clamp screws are loosened (keeping them snug to minimize unnecessary movement of the graft). The horizontal rod 57 is rotated to position the coring guide over the bone block. The coring guide is horizontal and parallel with the tendon. The guide is moved left/right to set the coring direction, then the clamp screw is tightened for the horizontal rod. The coring guide is brought down insuring that it comes in contact with the bone and is parallel to the tendon fibers. The clamp screw to secure the vertical rod is tightened at this time. Final adjustments to position are made, if needed.

The pneumatic oscillator/cutter 56 is assembled and inserted into the bushing 55 with the slot on the top. The cutter is not oscillated while the teeth are inside the bushing, but once it is past the bushing it is activated. The pneumatic oscillator/cutter is used to core through the bone block insuring that the slot is aligned with the top of the bone block. While holding tendon tight above, the cutter is gently advanced until the bone plug moves forward indicating that the cutter has cleared the bone block. The cutter is removed from the bone while oscillating. These steps are repeated for the other bone block.

Once the bone block is preshaped, the bone on the sides ("wings") of the tendon is removed, leaving the preshaped bone block attached to a wide tendon. See photographs of a graft made by the method of this application in FIGS. 13 and 14. The bone block can be separated from the tendon by cutting or tearing. Blunt or sharp dissection can be used.

All patents, test procedures, and other documents cited herein, including priority documents, are fully incorporated by reference to the extent such disclosure is not inconsistent with this application and for all jurisdictions in which such incorporation is permitted.

The invention claimed is:

1. An allograft or xenograft bone tendon bone graft comprising:
   a) a bone block having a width defined by two or more cut surfaces and a length,
   b) a tendon having a width defined by two or more natural or trimmed edges and a length,
   c) a natural attachment between said tendon and said bone block,
   d) two sides of said tendon defined by said two or more natural or trimmed edges;
wherein said natural attachment between said tendon and said bone block is maintained from the donor at both the end of said bone block and along at least a portion of both of said cut surfaces at the sides of said bone block;
wherein said width of said tendon is greater than said width of said bone block;
wherein said two sides of said tendon extends along the length of said tendon and beyond said length of said bone block in at least one direction;
wherein said tendon and said bone block are preshaped wherein at least a portion of said two sides of said tendon are folded or wrapped around at least a portion of both of said cut surfaces at the sides of said bone block; and
wherein said two sides of said tendon are configured to meet or substantially meet at the top of the graft when folded or wrapped.

2. The allograft or xenograft bone tendon bone graft of claim 1 wherein, at its widest point, the width of said tendon is at least 1.5 times the width of said bone block.

3. The allograft or xenograft bone tendon bone graft of claim 1 wherein said bone block comprises a cross-sectional profile selected from the group consisting of semi-circular, semi-ovular, triangular, polygonal, trapezoidal, rectangular, and square.

4. The allograft or xenograft bone tendon bone graft of claim 1 wherein said bone block comprises a further pre-shaped feature to accommodate said tendon when placing said graft in a human patient.

5. The allograft or xenograft bone tendon bone graft of claim 1 wherein said bone block comprises a further pre-shaped feature to aid in placement or fixation of the graft.

6. The allograft or xenograft bone tendon bone graft of claim 1 wherein said bone block comprises a tapered section.

7. The allograft or xenograft bone tendon bone graft of claim 1 wherein said natural attachment between said tendon and said bone block is maintained from the donor at both the end of said bone block and along the full length of both of said cut surfaces at the sides of said bone block.

8. The allograft bone tendon bone graft of claim 1 wherein said tendon comprises a patellar tendon, quadriceps tendon or Achilles tendon.

* * * * *